United States Patent
Lessmeier et al.

(10) Patent No.: US 8,145,306 B2
(45) Date of Patent: Mar. 27, 2012

(54) METHOD FOR OPTIMIZING CRT THERAPY

(76) Inventors: Timothy J. Lessmeier, Spokane, WA (US); Paul B. Gregerson, Spokane, WA (US)

( * ) Notice: Subject to any disclaimer, the term of this patent is extended or adjusted under 35 U.S.C. 154(b) by 872 days.

(21) Appl. No.: 12/228,848

(22) Filed: Aug. 18, 2008

(65) Prior Publication Data

US 2009/0099619 A1 Apr. 16, 2009

Related U.S. Application Data

(60) Provisional application No. 60/998,939, filed on Oct. 15, 2007.

(51) Int. Cl.
*A61B 5/04* (2006.01)
(52) U.S. Cl. .......................................................... 607/18
(58) Field of Classification Search .................. 600/518; 607/9
See application file for complete search history.

(56) References Cited

U.S. PATENT DOCUMENTS

| | | | |
|---|---|---|---|
| 6,597,951 B2 | 7/2003 | Kramer et al. | |
| 6,978,184 B1 | 12/2005 | Marcus et al. | |
| 7,194,306 B1 | 3/2007 | Turcott | |
| 2004/0059237 A1 | 3/2004 | Narayan et al. | |
| 2004/0225328 A1 | 11/2004 | Okerlund et al. | |
| 2004/0267326 A1 | 12/2004 | Ocel et al. | |
| 2006/0058647 A1* | 3/2006 | Strommer et al. | 600/434 |
| 2006/0095085 A1 | 5/2006 | Marcus et al. | |
| 2006/0224196 A1 | 10/2006 | Hettrick et al. | |
| 2006/0247692 A1 | 11/2006 | Yang et al. | |
| 2006/0253155 A1 | 11/2006 | Dingman et al. | |
| 2007/0027489 A1 | 2/2007 | Gill et al. | |
| 2007/0060961 A1 | 3/2007 | Echt et al. | |
| 2007/0060962 A1 | 3/2007 | Papone | |
| 2008/0260230 A1* | 10/2008 | Gotardo et al. | 382/131 |
| 2010/0331950 A1* | 12/2010 | Strommer | 623/1.11 |

* cited by examiner

Primary Examiner — Eric D. Bertram
(74) Attorney, Agent, or Firm — William A. Jeckle

(57) ABSTRACT

A method to optimize CRT therapy using ventricular lead motion analysis, either radiographically or with three dimensional electromagnetic mapping, to determine whether focal dyssynchrony is present at baseline, and whether biventricular pacing improves synchronicity and fractional shortening, and if no improvement is evidenced, changing the timing offset, pacing configuration and/or repositioning the ventricular leads to optimize effectiveness of CRT therapy. Various uses of this method include: diagnostic, with temporary leads to determine presence or absence of dyssynchrony and response to pacing; and therapeutic, to guide lead placement and programming during implant of CRT, and to optimize reprogramming of CRT during follow-up.

17 Claims, 9 Drawing Sheets

Synchronous lead tip Motion

Dyssynchronous lead tip Motion

X-ray Projections

Dynamic Lead Motion Analysis

METHOD FOR OPTIMIZING CRT THERAPY

RELATED APPLICATIONS

This application claims the benefit of U.S. Provisional Patent Application No. 60/998,939 filed on Oct. 15, 2007.

BACKGROUND OF THE INVENTION

1. Field of the Invention

This invention relates to surgery, and more particularly to a method for determining the synchronicity of ventricular contractions and optimizing the synchronicity of ventricular contractions during CRT therapy and during follow-up.

2. Background and Description of Prior Art

The human heart is a pump with four chambers that beat in an organized sequence. Anatomically the heart is divided into left and right sides, and upper and lower chambers. The two upper chambers are the atria and the two lower chambers are the ventricles.

In a cardiac cycle blood enters the heart from the body's venous system though the vena cava filling the right atrium. When the heart beats, the right atrium contracts forcing blood therein through the tricuspid valve into the right ventricle. Thereafter, contraction of the right ventricle forces the blood therein through the pulmonary artery to the lungs. Oxygenated blood returns to the heart, from the lungs, through the pulmonary vein and enters the left atrium. Contraction of the left atrium, which normally occurs synchronously with contraction of the right atrium, forces the blood therein through the mitral valve into the left ventricle. Contraction of the left ventricle, which normally occurs synchronously with contraction of the right ventricle, forces the blood therein outward through the aorta into the vascular system.

Systole is that portion of the cardiac cycle when the ventricular muscle cells contract causing the ventricles to force blood out of the ventricles to the lungs and body. Diastole occurs sequentially to systole and is that portion of the cardiac cycle when the ventricular muscle cells relax and the ventricles re-fill with blood from the atria.

Chamber synchrony is maintained by a complex conduction system which propagates electrical impulses to the heart muscle cells. The electrical impulses initiate the atrial and ventricular contractions.

The Sino-Atrial Node (SA node) is the pacemaker for the heart and is located in an upper portion of the right atrium. Electrical impulses spread from the SA node and cause adjacent atrial cells to depolarize in a spreading wave-front, causing the right and left atria to contract and pump blood into the respective ventricles. Depolarization and contraction of the left and right atria correlates with a "P wave" on an electrocardiogram (ECG). The electrical impulse continues propagating downwardly to the Atrio-Ventricular node (AV node) which is a small mass of highly specialized cardiac muscle fibers located in a lower portion of the right atrium. The AV node is the electrical connection from the right atrium to the right and left ventricles.

The AV node distally becomes the HIS bundle which bifurcates into a right bundle branch (RBB) and a left bundle branch (LBB). The bundle branches distally divide further into a network of Purkinje fibers which are specialized cells that conduct electrical impulses faster than other cells. Electrical impulses passing through the AV node continue through the bundle branches, and into the Purkinje fiber network encompassing the right and left ventricles. Because of the density of the Purkinje fiber network and the speed with which Purkinje fibers conduct electrical impulses, in a normal healthy heart, all the ventricular muscle cells contract synchronously during systole. Depolarization and contraction of the ventricles correlates with the "QRS" complex on an ECG. The synchronized contraction of the atria and ventricles enhances the heart's pumping power. Thus, the heart includes both a complex electrical network of specialized conduction tissues and a complex mechanical network of chambers and valves.

A variety of disorders prevent the heart from operating normally, and these disorders may be systolic or diastolic and may cause dyssynchrony as well as abnormal contractility. Some of these disorders are caused by degeneration of the left ventricular conduction system which may block conduction of the electrical impulses and/or may delay propagation of the electrical impulses to the heart muscle cells. For example, left or right bundle branch block (LBBB/RBBB) is a heart failure condition that occurs when the conduction of the electrical impulses to the left or right ventricle is blocked or slowed. Bundle branch block can cause dysschronous ventricular contractions which may result in heart failure. Intra-ventricular conduction delay (IVCD) is a heart failure condition that occurs when the propagation of the electrical impulses to the ventricles is "slowed down" by regional injury to myocardial tissue or by damaged Purkinje fibers that conduct the impulses slower than healthy Purkinje fibers.

When the left ventricular conduction system is damaged or "disconnected" the left ventricle muscle cells may still be excited eccentrically through muscle tissue conduction of the electrical impulses. Unfortunately, muscle tissue conduction is slower than Purkinje fiber network conduction and is also sequential. As a result, contraction of the affected portions of the left ventricle occurs in stages, rather than synchronously. For example, if a lateral wall of the left ventricle is affected by the conduction disorder, the muscle cells of the lateral wall will contract later than the muscle cells of the septal wall which is activated through normal Purkinje fiber conduction. Such dyssynchronous contraction degrades the contractility (pumping power) of the left ventricle and decreases the efficiency of the heart, which can result in, or exacerbate, heart failure.

Because the left ventricle pumps oxygenated blood to the body, a person's health is dependent upon the efficiency of the left ventricle. There are two primary methods of assessing the efficiency and pumping ability of the left ventricle; measuring Ejection Fraction, and measuring Shortening Fraction. Damage to the heart's electrical conduction system or damage to the heart's chambers and valves causes a decrease in Ejection Fraction and a decrease in Shortening Fraction.

Ejection Fraction measures the difference in the volume of blood within the left ventricle at the diastolic state, and at the systolic state, and compares the two volumes as a percentage. A normal Ejection Fraction range is 63-77% for males and 55-75% for females. Ejection Fraction percentage is determined with the following formula:

$$\frac{\left(\frac{\text{Left Ventricle Diastolic Volume} -}{\text{Left Ventricle Systolic Volume}}\right) \times 100}{\text{Left Ventricle Diastolic Volume}}$$

Shortening Fraction percentage measures the change in the diameter of the left ventricle between the systolic state and the diastolic state and is determined with the following formula:

$$\frac{\left(\text{Left Ventricle End-Diastolic Diameter} - \text{Left Ventricle End-Systolic Diameter}\right) \times 100}{\text{Left Ventricle End} - \text{Diastolic Diameter}}$$

A Shortening Fraction greater than 30% is considered normal. A decrease in shortening fraction usually precedes a decrease in ejection fraction.

Cardiac Resynchronization Therapy (CRT), also called biventricular pacing, has been shown to improve the symptoms of ventricular dysschrony and abnormal contractility and improve heart failure symptoms. CRT uses biventricular pacing to synchronize left ventricular contraction by sending electrical impulses to the heart through surgically implanted electrical leads. CRT is currently indicated for patients with left ventricular systolic dysfunction, an ejection fraction of less than 35%, a prolonged QRS complex of >120 msec and severe heart failure (New York Heart Association classification III and IV) despite maximal medical therapy.

Unfortunately, only about 65% to 70% of patients respond positively to CRT and the lack of positive response may be due to sub-optimal lead placement. Sub-optimal lead placement may occur because there is presently no dynamic testing of the lead positions to determine physiologic response to CRT. Further, testing of the lead positions is not performed to provide baseline measures of ventricular dysschrony, contractility or fractional shortening. As a result it is difficult to assess whether there is baseline dyssynchrony and whether there is improvement in ventricular synchronicity, contractility and fractional shortening with current CRT implant techniques using empirically positioned leads.

What is needed is a method to optimize the benefits of CRT therapy, to ensure optimal lead placement by dynamic assessment of lead locations during intrinsic or baseline rhythm and during biventricular paced rhythm and to provide objective measures to determine procedure effectiveness.

Our method for optimizing CRT therapy resolves various of the aforementioned drawbacks. Our method provides a tool for practitioners to objectively determine whether biventricular pacing provides physiologic benefits to the patient by allowing dynamic assessment of the motion of the ventricular leads, and therefore the motion of the ventricle walls, and provides measures of dyssynchrony, contractility and fractional shortening. The provided measures allow assessment during intrinsic heart rhythm, to establish baseline focal dyssynchrony and fractional shortening, as well as biventricular paced heart rhythm to determine focal physiologic response to CRT therapy (i.e. changes in focal dyssynchrony and fractional shortening). Our method can be utilized prognostically as a test for focal dysschrony and response to pacing at temporary lead locations and with differing pacing configurations, and for optimizing CRT therapy at implant. Our method allows optimization of lead position to improve patient outcomes based on physiologic assessment during the CRT procedure and during follow-up.

Our invention does not reside in any one of the identified features individually but rather in the synergistic combination of all of its features, which give rise to the functions necessarily flowing therefrom as hereinafter specified and claimed.

SUMMARY

A method to optimize CRT therapy having the steps of implanting ventricular leads in a patient's heart; one application of the method involves radiologically scanning the heart over the duration of plural cardiac cycles during intrinsic heart rhythm and during biventricular paced rhythm in multiple views; determining X, Y and Z axis coordinate positional data of the ventricular leads relative to time; exporting the positional data to an analysis program for plotting and comparison of the movement of the implanted ventricular leads; determining the movement of the ventricular walls based upon the motion of the ventricular leads; comparing the intrinsic ventricular wall movement data to the paced ventricular wall movement data to assess baseline dyssynchrony and fractional shortening to determine whether pacing has improved synchronicity and fractional shortening, and if no improvement is evidenced changing the timing offset and/or repositioning the ventricular leads to another position in the heart to optimize the effectiveness of the CRT therapy. Another application of the method involves utilizing three dimensional mapping systems (such as St Jude NAVX) to delineate lead tip motion similarly allowing evaluation of baseline and paced synchronicity and fractional shortening.

In providing such a method it is:

a principal object to provide a method to optimize CRT therapy by evaluating and analyzing motion of the surgically implanted ventricular leads a further object to provide a method to assess baseline ventricular synchronicity.

a further object to provide a method to dynamically assess paced ventricular synchronicity.

a further object to provide a measure of focal dyssynchrony.

a further object to provide a measure of focal contractility.

a further object to provide a method for optimizing ventricular lead placement to improve CRT therapy outcome based on physiologic assessment.

a further object to determine whether a patient will benefit from CRT therapy by testing lead locations during the CRT implantation.

a further object to provide a pre-procedure diagnostic test to predict CRT response.

a further object to avoid ineffective placement of biventricular leads.

a further object to provide a method to determine movement of ventricular walls in three dimensions.

a further object to provide a method to graphically show movement of ventricular walls.

a further object to improve ventricular synchrony, improve heart failure symptoms, reverse remodeling, improve ejection fraction, and decrease risk of dying.

a further object to provide a method to measure focal shortening fraction.

a further object to provide a method to measure focal dyssynchrony.

a further object to provide a prognostic test for focal dyssynchrony and for response to pacing at temporary lead tip locations.

a still further object to provide a method for prognostic evaluation of dyssynchrony and response to biventricular pacing, and for optimizing CRT therapy by dynamically evaluating lead locations that is of new and novel design that maximizes physiologic benefits, reduces cost, improves the patient's health, prevents ineffective CRT implant placement and one that is otherwise well suited to the uses and purposes for which it is intended.

Other and further objects of our invention will appear from the following specification and accompanying drawings which form a part hereof. In carrying out the objects of our invention it is to be understood that the method, apparatus, steps and procedures are susceptible to change in design and arrangement with only one preferred and practical embodiment of the best known mode being illustrated in the accompanying drawings and specified as is required.

BRIEF DESCRIPTIONS OF DRAWINGS

In the accompanying drawings which form a part hereof and wherein like numbers refer to similar parts throughout:

DESCRIPTION OF PREFERRED EMBODIMENT

Figure 1:
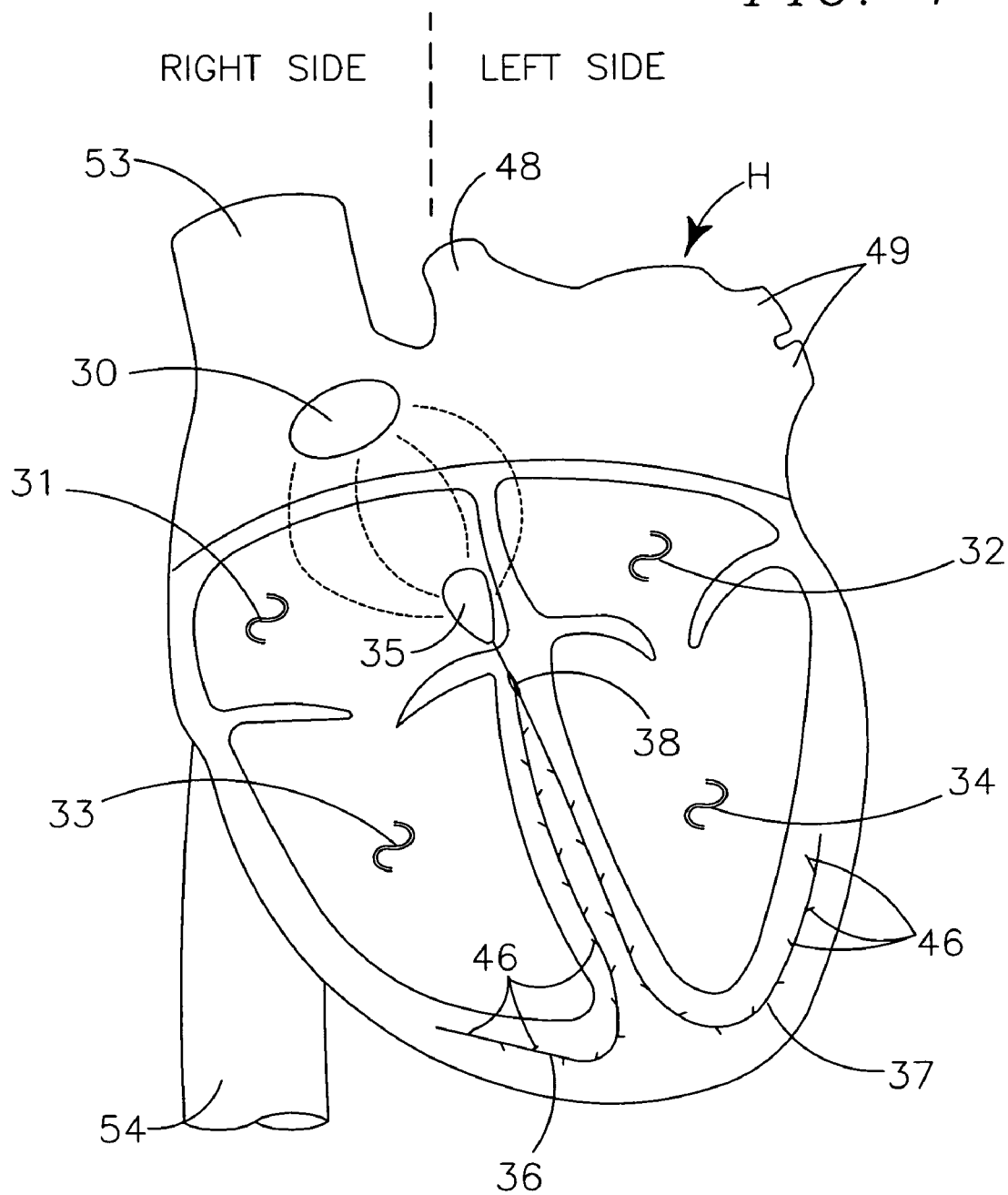
FIG. 1 is a diagrammatic representation of a human heart showing the heart chambers and portions of the electrical impulse conduction system.

The present invention provides a method for optimizing cardiac resynchronization therapy (CRT) by assessing movement of tips of ventricular leads implanted in a human heart. The disclosed method is expressly described in terms of the left ventricle; however application to the other heart chambers, including the right ventricle, may be readily appreciated by those skilled in the art without departing from the present inventive method.

Our method generally provides a ventricular pacemaker 20 having a left ventricular lead 21, a right ventricular lead 22 and an atrial lead 23; a radiological three dimensional imaging system 24; an image compiling system 25; an analytical processing system 27 and a visual display 26. The left ventricular lead 21 has a lead tip 21a at its terminal end, the right ventricular lead 22 has a lead tip 22a at its terminal end and the atrial lead 23 has a lead tip 23a at its terminal end.

CRT is currently indicated for patients with left ventricular dyssynchrony, an ejection fraction<35%, a prolonged QRS complex 43 having a duration>120 msec and severe heart failure, New York Heart Association (NYHA) classification III or IV, despite maximal medical therapy.

The normal cardiac conduction system is diagramed at FIG. 1. The sinoatrial node 30 (SA node) proximate the right atrium 31 is the pacemaker for heart H. Electrical impulses are generated in and propagate from the SA node 30 to synchronously activate cardiac muscle cells comprising right atrium 31 and left atrium 32. The electrical impulse then propagates downwardly to atrioventricular node 35 (AV node) which is the electrical connection from the right atrium 31 to right ventricle 33 and left ventricle 34.

Figure 7:
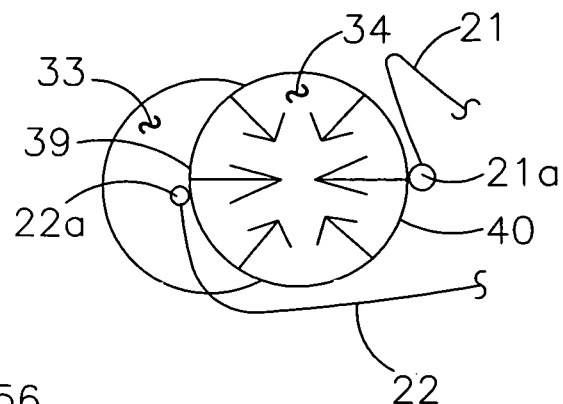
FIG. 7 is a diagrammatic cross-section of the right and left ventricles showing positions of the ventricular lead tips as shown by a left anterior oblique (LAO) x-ray view with arrows representing synchronous ventricular wall movement.
Figure 8:
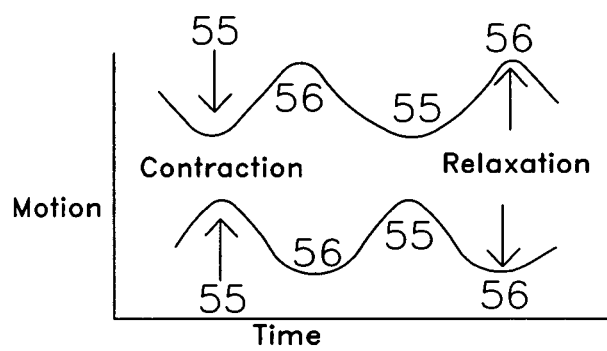
FIG. 8 is a graphic representation correlating with FIG. 7 of movement of the right (bottom line) and left (top line) ventricular lead tips, relative to each other, during synchronous ventricular contraction.

The AV node 35 distally becomes HIS bundle 38 which bifurcates into left bundle branch 37 and right bundle branch 36 which conduct the electrical impulse to Purkinje fibers 46 of the right ventricle 33 and the left ventricle 34 so that electrical activation of the right ventricle 33 and left ventricle 34 occurs synchronously resulting in uniform ventricular contraction. (FIGS. 7, 8).

Figure 4:
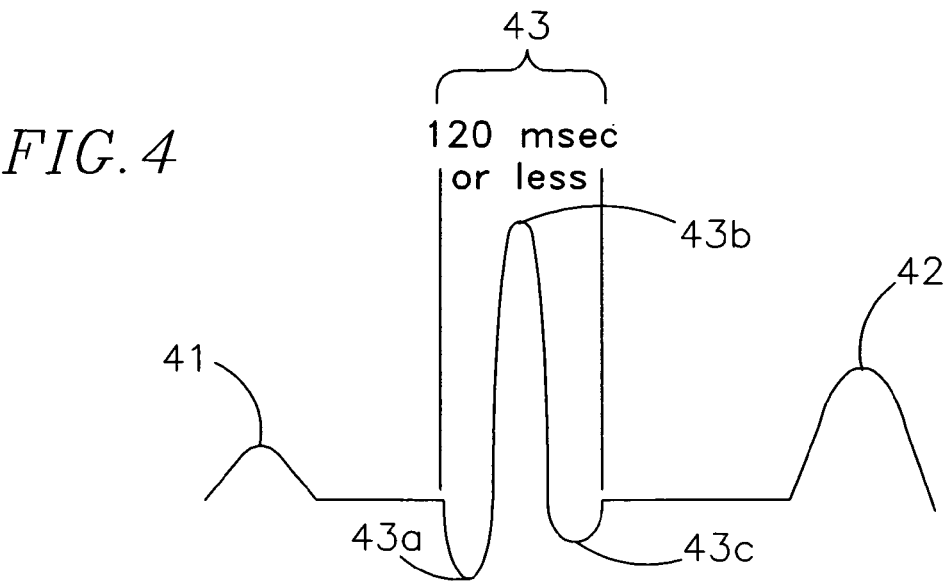
FIG. 4 is a diagrammatic ECG recording of a normal cardiac cycle showing a P-wave, a T-wave and a QRS complex having a duration of <120 msec.
Figure 5:
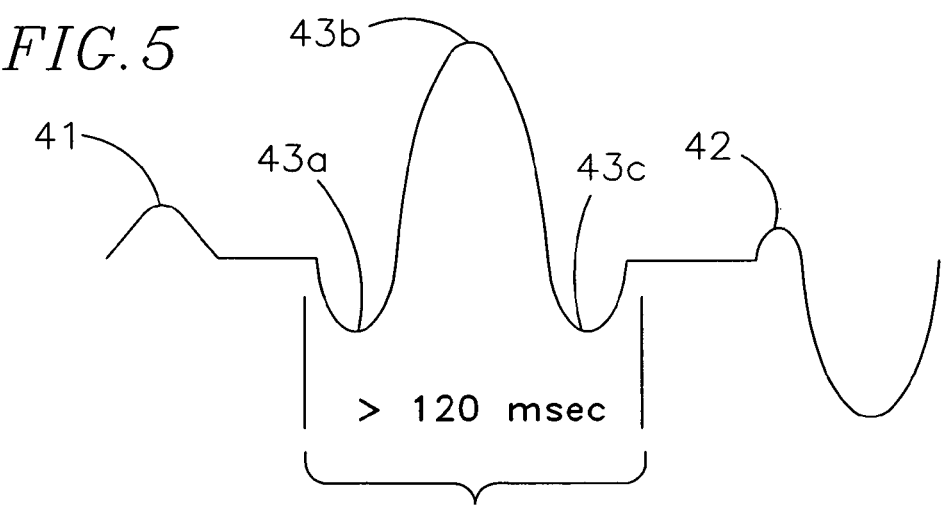
FIG. 5 is a diagrammatic ECG recording of an abnormal cardiac cycle showing a prolonged QRS complex of >120 msec.

Cardiac muscle cells (not shown) need to be electrically excited to undergo mechanical contraction. During the excitation, known as depolarization, electrical signals are generated that can be recorded with an electrocardiogram (ECG) (not shown). Features of an ECG recording (FIGS. 4, 5) correspond to the origin of the electrical activity. Depolarization in the atria 31, 32 generates a P wave 41. Depolarization in the ventricles 33, 34 generates a wave form known as a QRS complex 43 which consists of a Q-wave 43a, an R-wave 43b and an S-wave 43c. A normal QRS complex 43 has a duration of less than 120 msec. (FIG. 4). A QRS complex 43 having a duration greater than 120 msec (FIG. 5) is abnormal and is one criteria for CRT.

Figure 9:
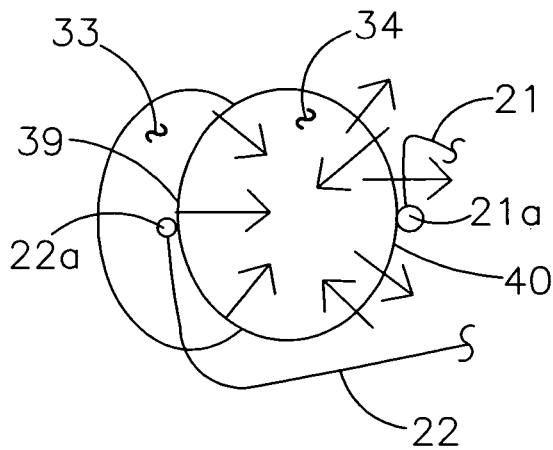
FIG. 9 is a diagrammatic cross-section of the right and left ventricles showing positions of the ventricular lead tips as shown by a left anterior oblique (LAO) X-ray view with arrows representing dyssynchronous ventricular wall movement.
Figure 10:
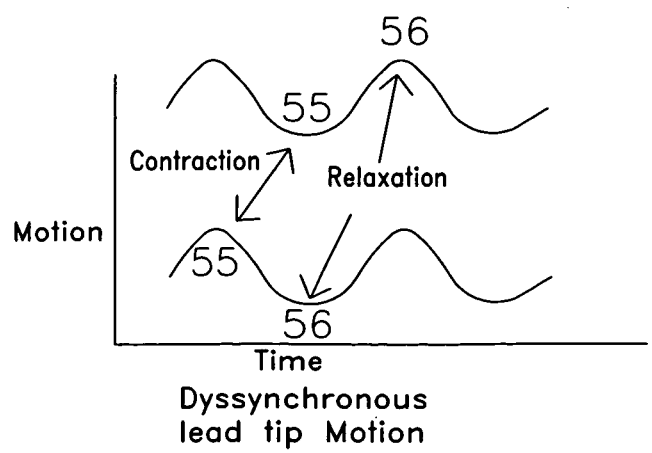
FIG. 10 is a graphic representation correlating with FIG. 9 of movement of the right (bottom line) and left (top line) ventricular lead tips, relative to each other, during dyssynchronous ventricular contraction.

Damage to the conduction tissues below the AV node 35, such as at the level of the bundle branches 36, 37 or lower, can result in dyssynchronous activation of the ventricles 33, 34 which may lead to ventricular dysschrony. Ventricular dysschrony is defined as non-uniform contraction of the ventricles 33, 34 due to delayed activation. (FIGS. 9, 10). Damage to the conduction tissues may also cause a prolonged QRS complex 43. Current guidelines use a prolonged QRS complex 43 as a surrogate to identify ventricular dyssynchrony. Unfortunately, a prolonged QRS duration and ventricular dyssynchrony only show a rough correlation to one another.

Figure 2:
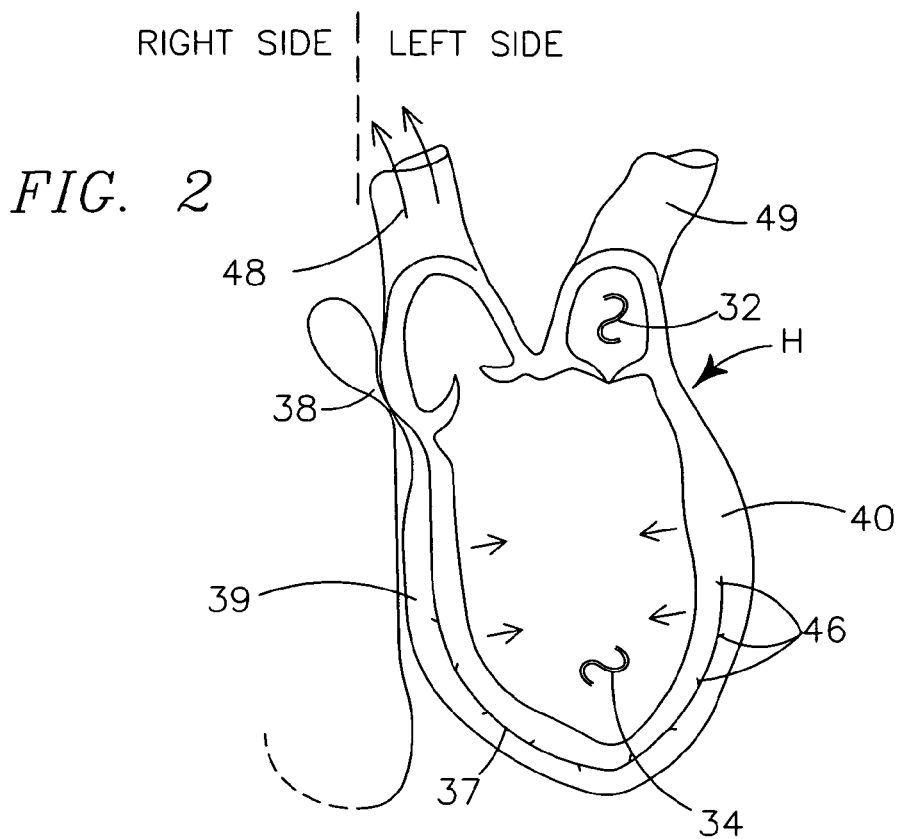
FIG. 2 is a diagrammatic representation of the left ventricle beginning contraction.
Figure 3:
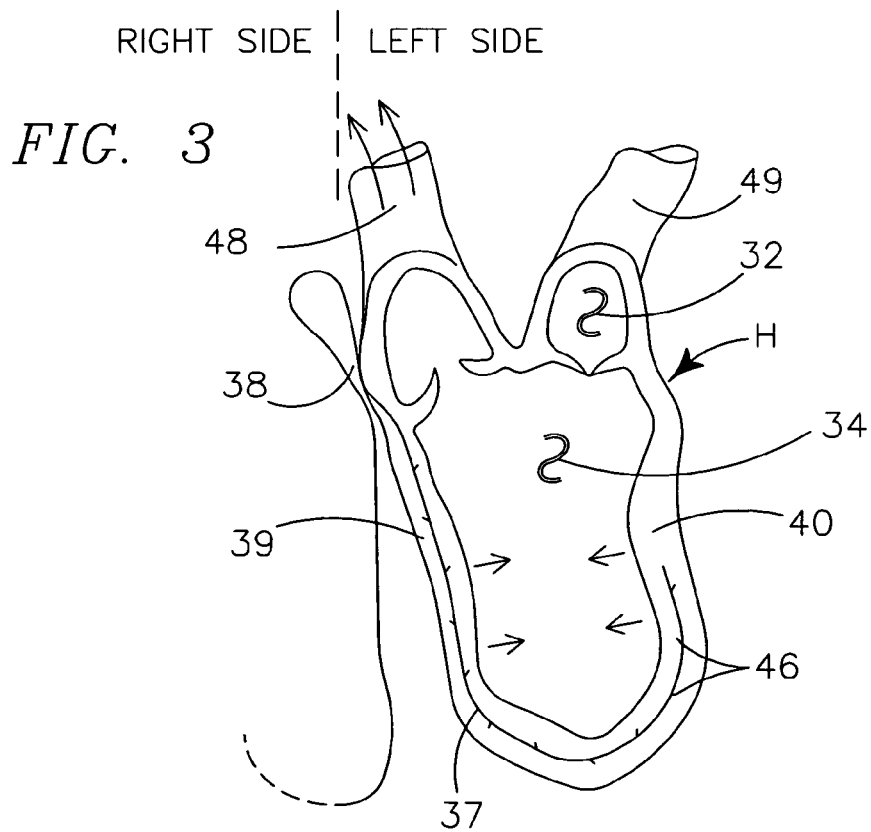
FIG. 3 is a diagrammatic representation similar to that of FIG. 2 showing the left ventricle in its contracted state.

As shown in FIGS. 2 and 3, the left ventricle 34 starts to contract after an electrical impulse (not shown) propagating down from the left bundle branch excites muscle cells (not shown) of septal wall 39 and lateral wall 40. As the muscle cells contract they become shorter and thicker causing the septal and lateral walls 39 and 40 respectively, to contract inwardly towards each other to pump blood out of the left ventricle 34 to the body (not shown) through the aorta 48.

Figure 6:
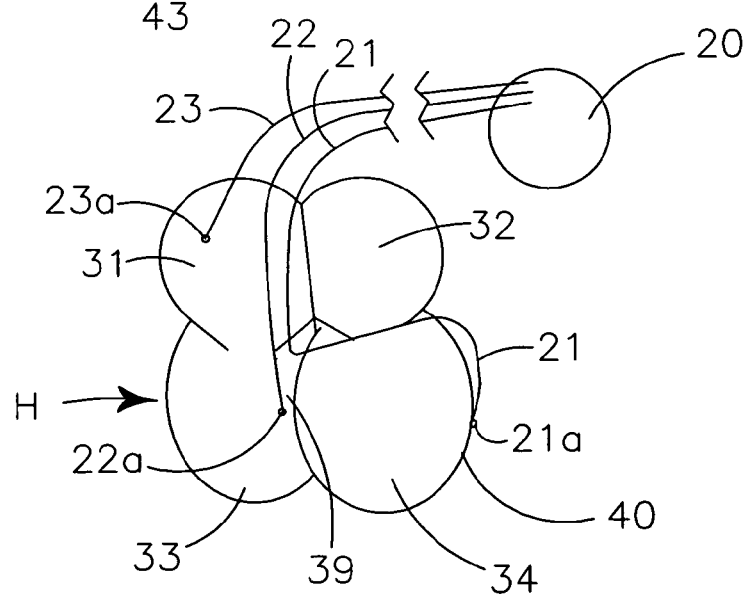
FIG. 6 is a diagrammatic representation of a human heart showing a biventricular pacing mechanism having leads communicating with the right atrium, right ventricle and left ventricle.

As shown in FIG. 6, CRT uses an atrial lead 23 having a lead tip 23a positioned in the right atrium 31, a right ventricular lead 22 having a lead tip 22a positioned on right ventricular apex or septal wall 39 and a left ventricular lead 21 having a lead tip 21a implanted on left ventricular lateral wall 40, left ventricular anterolateral wall (not shown) or left ventricular posterolateral wall (not shown) to provide pacing on both sides of the left ventricle 34 to resynchronize left ventricle 34 activation.

Figure 17:
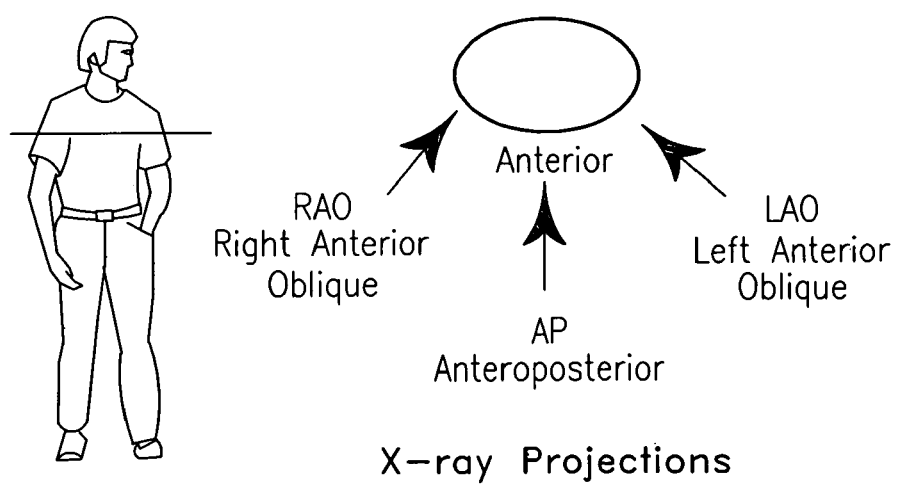
FIG. 17 is a diagrammatic representation of the three X-ray projections used for cine loop recordings.

FIGS. 7 and 9 represent a cross-section view of the right ventricle 33 and left ventricle 34 similar to a left anterior oblique (LAO) X-ray view (FIG. 17) and show the relative positions of the right ventricular lead tip 22a and the left ventricular lead tip 21a. Arrows represent direction of ventricular wall movement during synchronous systole/contraction (FIG. 7) and dysschronous systole/contraction (FIG. 9).

FIGS. 8 and 10 are graphic representations of the motion of the left ventricular lead tip 21a and the motion of the right ventricular lead tip 22a in the short axis shown in FIGS. 7 and 9. FIGS. 7 and 8 show normal synchronous ventricular contraction while FIGS. 9 and 10 show dyssynchronous ventricular contraction evidenced by a timing difference of the left ventricular lead tip 21a and right ventricular lead tip 22a at maximum contraction 55 and relaxation 56. As shown, maximal contraction 55 of the left ventricular lead tip 21a occurs at a trough in the graphic representation of the lead tip movement and is 180 degrees out of phase as compared to the maximal contraction 55 of the right ventricular lead tip 22a which occurs at a crest in the graphic representation of the lead tip movement.

Figure 11:
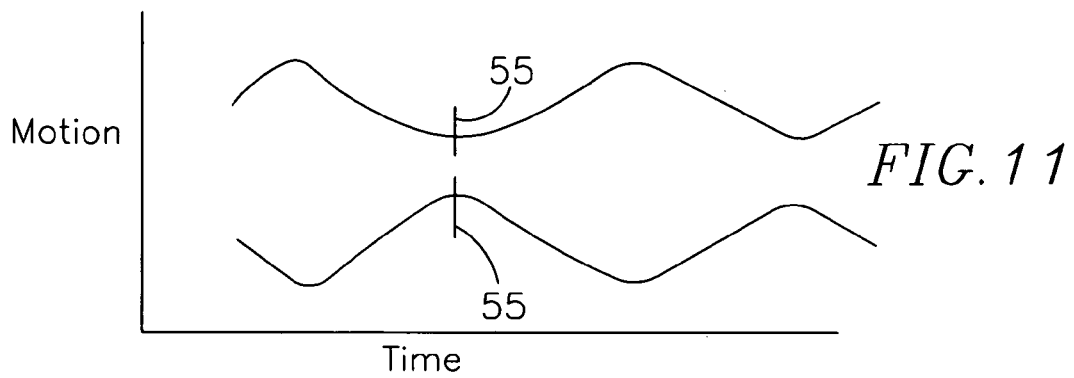
FIG. 11 is a graphic representation of synchronous left ventricular contraction showing focal synchrony; left ventricular lead motion is depicted on the top with the right ventricular lead motion depicted on the bottom.
Figure 12:
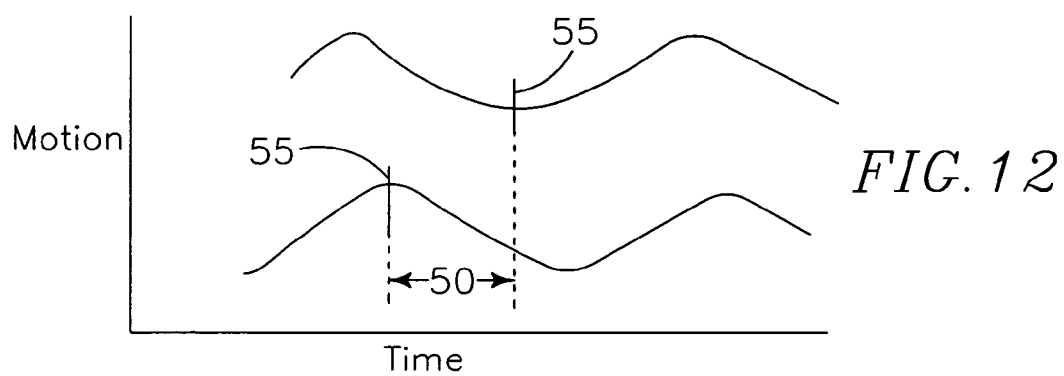
FIG. 12 is a graphic representation of dyssynchronous left ventricular contraction showing focal dyssynchrony with left ventricular lead motion depicted on the top and right ventricular lead motion depicted on the bottom.

FIGS. 11 and 12 are lead tip 21a, 22a motion schematics. Synchronous ventricular contraction (FIG. 11) is evidenced by simultaneous (vertically aligned) right ventricular lead tip 22a and left ventricular lead tip 21a maximal contraction 55. Dyssynchronous ventricular contraction (FIG. 12) is evidenced by a timing delay 50 between maximal contraction 55 of the lead tips 21a, 22a.

The difference in time 50 to maximal contraction 55 of the right ventricular lead tip 22a and left ventricular lead to 21a is a focal measure of dyssynchrony. FIG. 12 illustrates this measurement at 50. The difference in time 50 from onset of electrical activation (start of the QRS complex 43) to maximal contraction 55 of the right or left ventricular lead (not shown), also provides a measure of electromechanical dyssynchrony.

Figure 13:
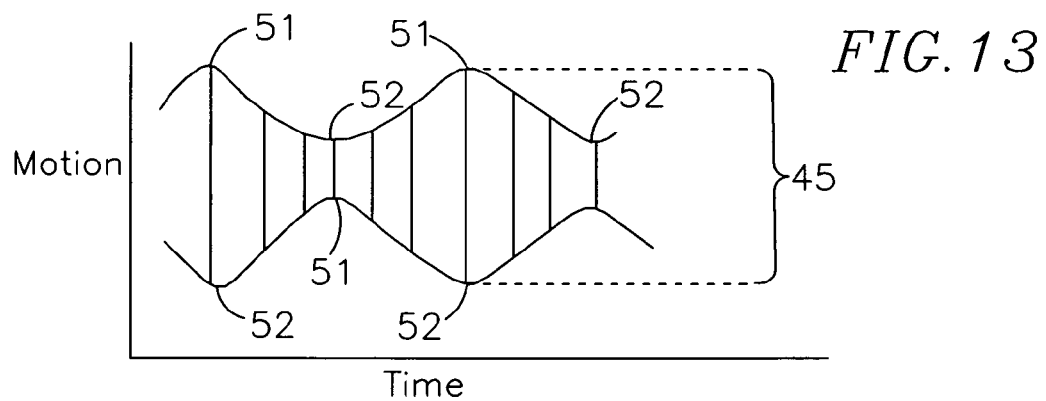
FIG. 13 is a graphic representation of synchronous left ventricular contraction showing normal contractility with left ventricular lead motion depicted on the top and right ventricular lead motion depicted on the bottom.
Figure 14:
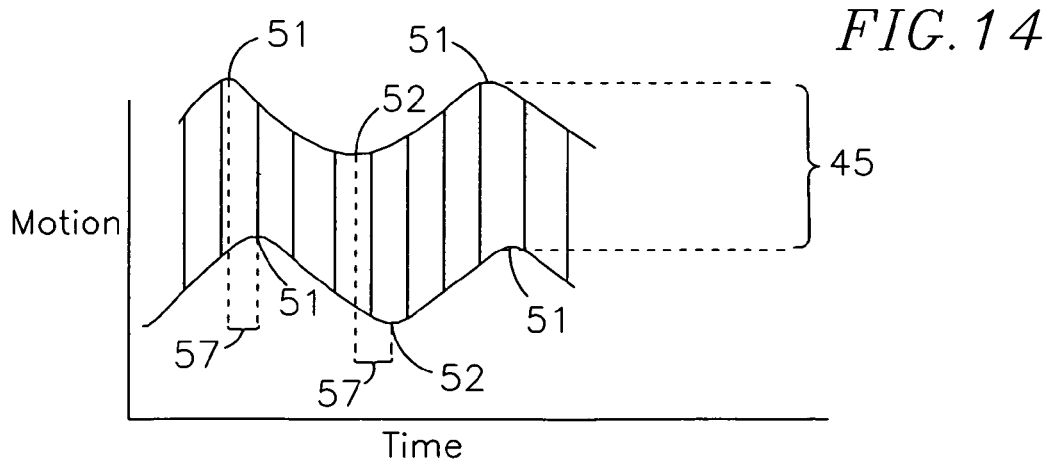
FIG. 14 is a graphic representation of dyssynchronous left ventricular contraction showing reduced contractility with left ventricular lead motion depicted on the top and right ventricular lead motion depicted on the bottom.

FIGS. 13 and 14 illustrate quantification of focal contractility by measuring the distance between the right ventricular lead tip 22a and the left ventricular lead tip 21a at time stamped points in a cardiac cycle. Average vertical distance 45 (FIGS. 13, 14) between the lead tips 21a, 22a at the same time stamp is the measure of focal contractility. FIG. 13 shows normal contractility represented by vertically aligned troughs 52 and crests 51 that are widely separated vertically while FIG. 14 shows reduced contractility represented by lessened vertical separation between the lead tips 21a, 22a at the same time stamp caused by ventricular dysschrony 50. Using contractility measures, fractional shortening may also be determined.

Figure 15:
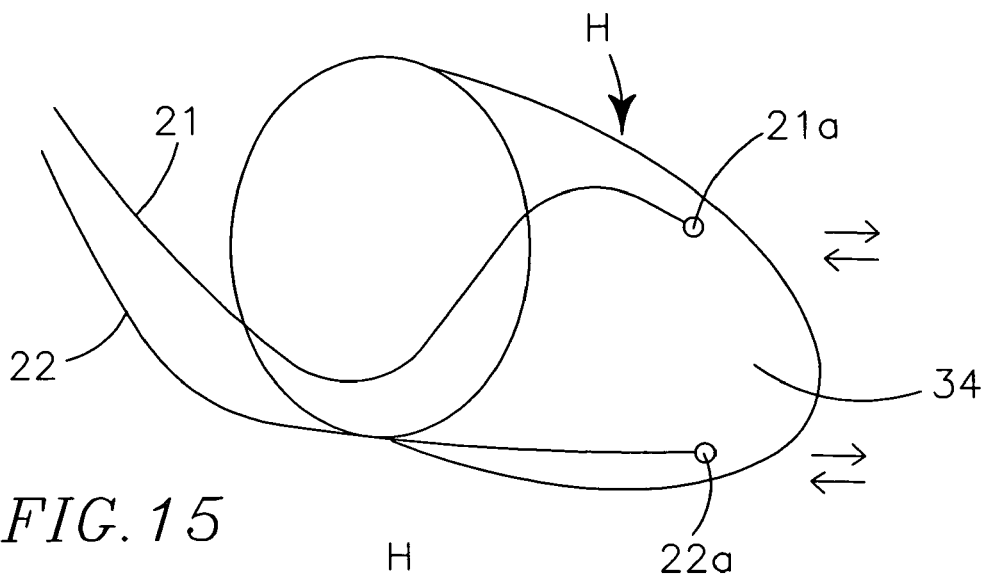
FIG. 15 is a diagrammatic representation of the left ventricle roughly correlating with a right anterior oblique (RAO) X-ray view with arrows showing longitudinal Z-axis motion of the ventricular lead tips during synchronous left ventricular contraction.
Figure 16:
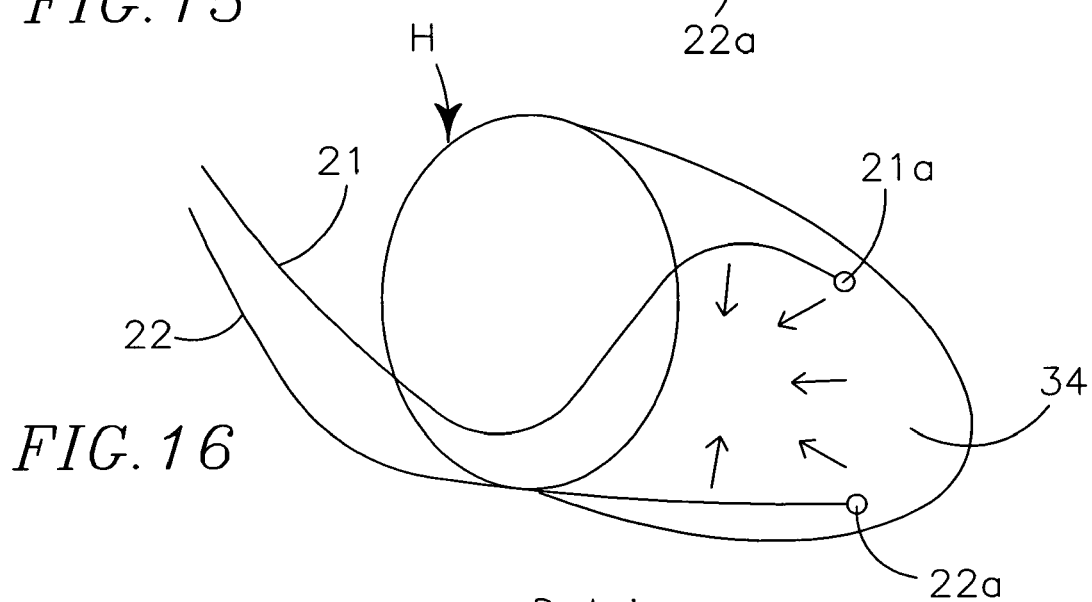
FIG. 16 is a diagrammatic representation of the left ventricle roughly correlating with a right anterior oblique (RAO) X-ray view with arrows showing longitudinal Z-axis motion of the ventricular lead tips during dyssynchronous left ventricular contraction.

Analysis of lead tip 21a, 22a motion in the left ventricular short axis (approximated in the LAO projection) provides data on concentric contraction and radial motion. (FIGS. 7, 9). Left ventricular lead tip 21a and right ventricular lead tip 22a motion in the RAO view provides data to determine longitudinal (Z-axis) motion. Synchronous Z-axis contraction and synchronous Z-axis relaxation of the ventricles 33, 34 is evidenced by parallel lines of motion for the right ventricular lead tip 22a and left ventricular lead tip 21a (FIG. 15) while dyssynchronous Z-axis contraction and dyssynchronous Z-axis relaxation is evidenced by non-parallel lines of motion for the right ventricular lead tip 22a and left ventricular lead tip 21a. (FIG. 16).

With radiologic analysis a cine loop recording (not shown) is made in left anterior oblique (LAO), right anterior oblique (RAO) and anterior posterior (AP) projections (FIG. 17) during plural complete cardiac cycles to document motion of the left ventricular lead tip 21a and the right ventricular lead tip 22a during intrinsic heart rhythm as well as during paced heart rhythm.

The cine loop recording data is exported, preferably in an AVI format, to the image compiling system 25 which is preferably a physics motion analysis program 25 such as Tracker™ software from Open Source Physics, Inc. wherein the X-axis, Y-axis and Z-axis coordinates for the left ventricular lead tip 21a and the right ventricular lead tip 22a are determined for each recorded cine frame and identified by time stamps throughout the plural cardiac cycles. Cine is no less than 15-30 frames per second (fps) to ensure accurate time stamps.

Table 1 sets forth a sample of the data collected by the physics motion analysis program 25 showing left ventricular lead tip 21a positions. For each position the cine frame time is noted as is the X-axis coordinate and the Y-axis coordinate.

TABLE 1

| t | x | y |
|---|---|---|
| 0 | 116.426 | 22.788 |
| 0.066 | 115.926 | 17.283 |
| 0.132 | 112.422 | 20.285 |

Figure 18:
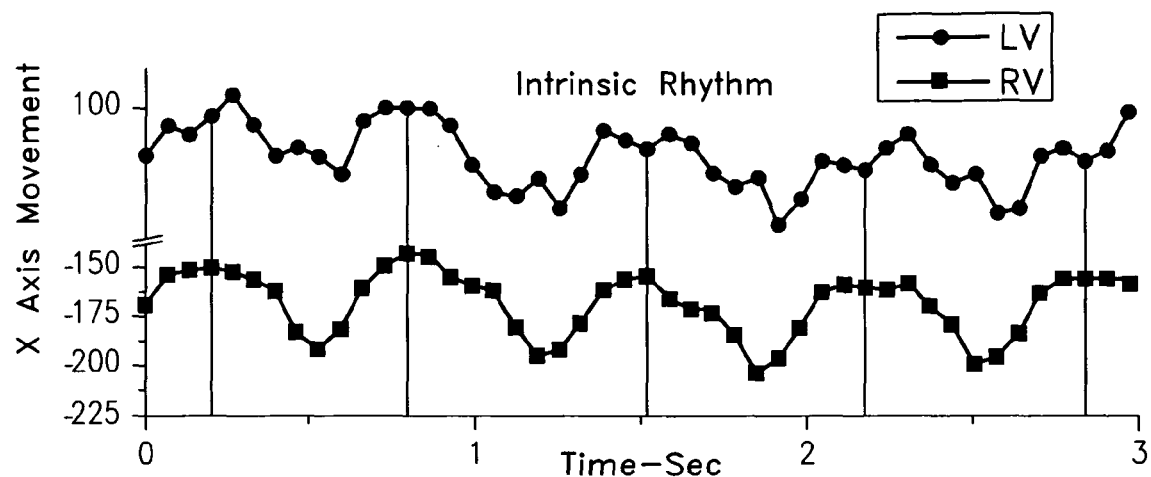
FIG. 18 is a graphic representation of dyssynchronous lead tip movement during intrinsic heart rhythm.
Figure 19:
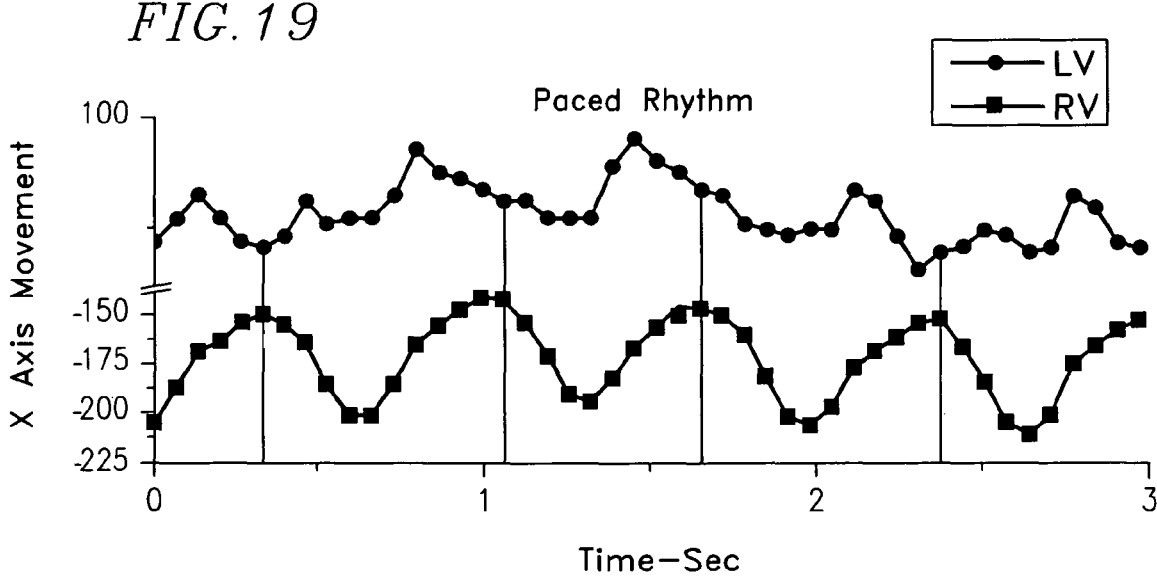
FIG. 19 is a graphic representation of paced lead tip movement showing improved synchrony.
Figure 20:
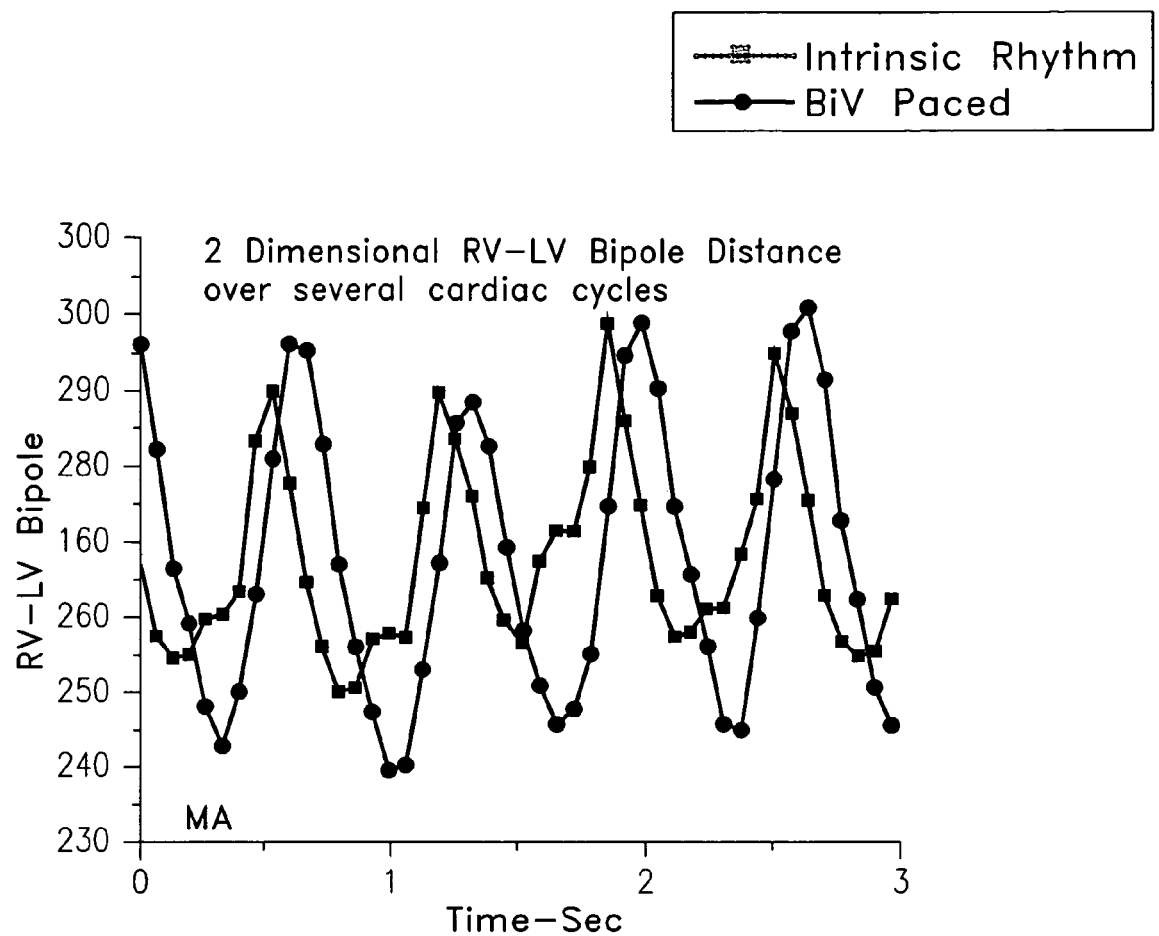
FIG. 20 is a graphic representation showing two dimensional ventricular lead tip movement along the X-axis and Y-axis during intrinsic heart rhythm and during paced heart rhythm showing improved contractility and improved shortening fraction during pacing.
Figure 21:
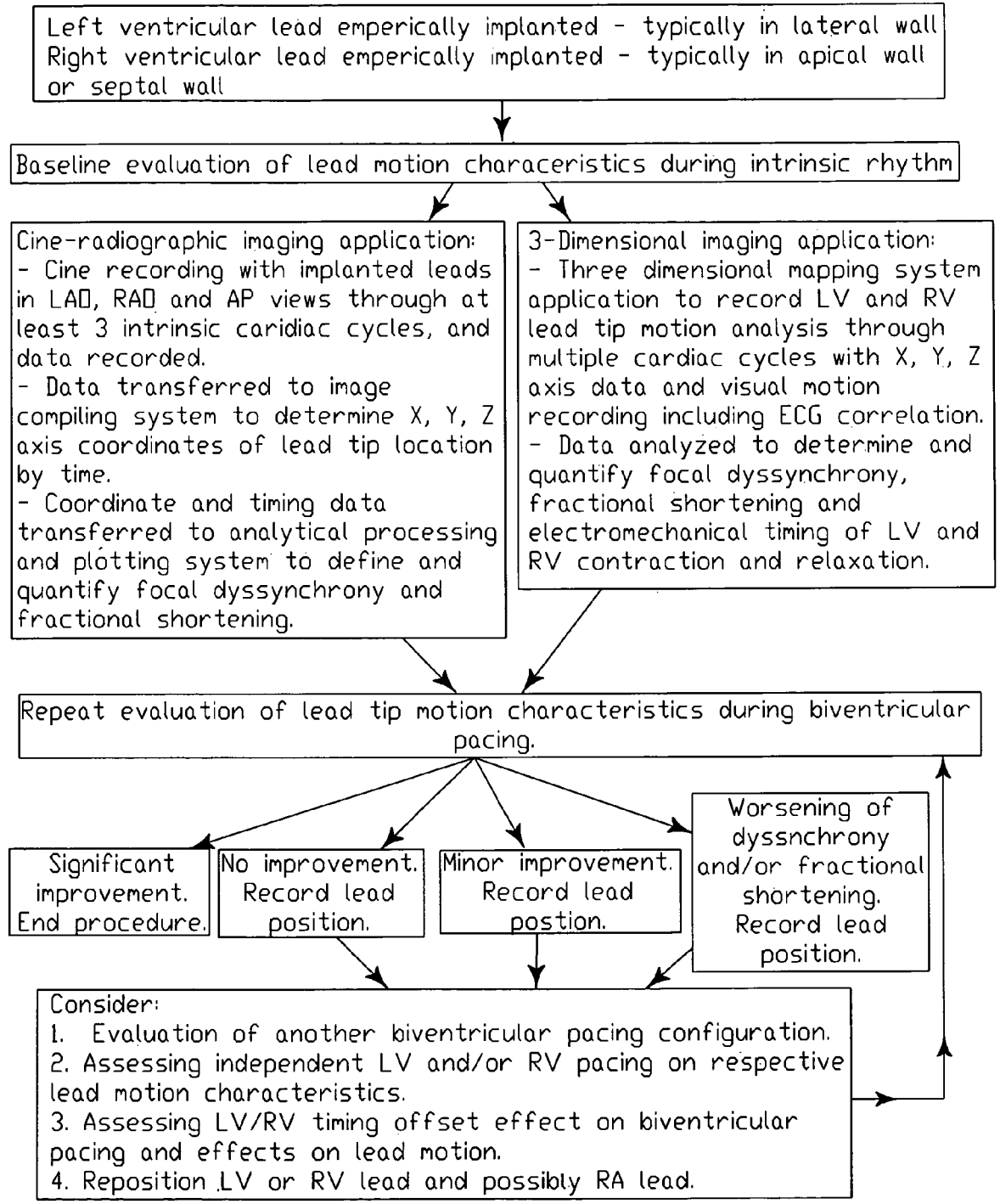
FIG. 21 is a flow chart setting forth the steps of the disclosed method for optimizing CRT therapy.

The X axis coordinate data, the Y axis coordinate data and the time data for each lead tip 21a, 22a, 23a in each view is then exported to analytical processing system 27 having a computer operating Origin™ software manufactured by Origin Lab Corp. of Northhampton, Mass., USA. Paired analyses comparing the intrinsic heart rhythm data and the paced heart rhythm data, is performed for each radiographic view. (LAO, RAO and AP). The motion of the left ventricular lead tip 21a and the motion of the right ventricular lead tip 22a motion is then visually presented, such as by graphing, showing the time difference 50 to maximum contraction 55 between the right ventricular lead tip 22a and left ventricular lead tip 21a which provides a focal measure of dysschrony (FIGS. 11, 12) and the percentage of shortening from maximum diastole to maximal systole between the left ventricular lead tip 21a and the right ventricular lead tip 22*a* providing a measure of contractility and shortening fraction. Baseline dysschrony, baseline contractility and baseline shortening fraction are then compared with paced dysschrony, paced contractility and paced shortening fraction at the current lead 21, 22 positions to determine the effectiveness of CRT. (FIGS. 18-20). Using the measures it is possible to assess whether there is focal improvement in dysschrony, contractility and shortening fraction with pacing at the current lead locations and pacing configuration. Other pacing configurations such as isolated right ventricular or left ventricular pacing, or pacing with RV-LV offset could also be similarly assessed.

This method is also applicable using a three dimensional mapping system such as St Jude Medical NAVX to document lead tip motion without x-ray use. In such an application, 3D mapping patches are placed for standard use and the left and right ventricular leads 21, 22 are connected to the NAVX monitor allowing 3-Dimensional recording of the motion of the monitored lead tips 21*a*, 22*a* during multiple cardiac cycles during intrinsic and paced rhythm. This technique allows correlation with ECG and allows measurement of electromechanical intervals (time from onset of QRS complex to peak contraction) of either lead 21, 22 and limits respiratory interference.

FIG. 18 shows dysschronous lead tip 21*a*, 22*a* movement during intrinsic heart rhythm at a plurality of time stamps. FIG. 19 shows motion of the lead tips 21*a*, 22*a* during paced rhythm at a plurality of time stamps showing improvement and more synchronous ventricular contraction 55.

In the absence of an ECG recording, systole is defined as earliest maximal contraction 55 of either ventricular lead tip 21*a*, 22*a* or in the case of severe akinesis, by the maximal two dimensional shortening between the two ventricular lead tips 21*a*, 22*a*. Similarly, diastole is defined as earliest maximal relaxation of either ventricular lead tip 21*a*, 22*a* or in the case of severe akinesis, by the maximal two dimensional lengthening between the ventricular lead tips 21*a*, 22*a*. When ECG recording is available, electromechanical intervals can be determined such as the onset of QRS to peak contraction of the left or the right ventricular lead tips 21*a*, 22*a* respectively.

Left ventricle lead tip 21*a* motion and right ventricle lead tip 22*a* motion are assessed in the LAO view during intrinsic heart rhythm. The position of both lead tips 21*a*, 22*a* is identified at each time stamped cine frame using the image compiling system 25. The lead tip 21*a*, 22*a* positions are documented at time intervals in two-dimensions (the X-axis correlates roughly with the short axis of the left ventricle 34 in the LAO view; the Y-axis, although also in the short axis of the left ventricle 34, correlates more directly with respiratory cardiac motion). The lead tip 21*a*, 22*a* motion data is then transferred to the analytical processing system 27.

In the X-axis, the motion of the left ventricular lead tip 21*a* and motion of the right ventricular lead tip 22*a* is plotted showing systole and diastole, lead excursion and the relation of right ventricle 33 to left ventricle 34 upon contraction 55. The time differential 50 from maximal right ventricle 33 contraction 55 to maximal left ventricle 34 contraction 55 is used to quantify local dyssynchrony 50. (FIG. 11, 12). A zero timing difference (FIG. 11) is consistent with synchronous ventricular contraction 55. A positive timing difference indicates right ventricle 33 maximal contraction 55 precedes left ventricle 34 maximal contraction 55 while a negative timing difference indicates left ventricle 34 maximal contraction 55 precedes right ventricle 33 maximal contraction 55. (FIG. 12). Multiple measurements are taken and averaged for consistency.

In two-dimensional analysis (FIGS. 13, 14 and 20) fractional shortening is determined for each contractile cycle. Fractional shortening is a measure of heart contractility and is measured using two-dimensional LAO view data to calculate the maximal distances between the lead tips 21*a*, 22*a* at the start and end of each cardiac cycle using the following formula: Shortening Fraction (%)=(maximal distance from right ventricle lead tip 22*a* to left ventricle lead tip 21*a*−minimal distance from right ventricle lead tip 22*a* to left ventricle lead tip 21*a*)×100/(maximal distance from right ventricle lead tip 22*a* to left ventricle lead tip 21*a*).

The distance measurements are repeated and assessed during biventricular pacing, during right ventricular pacing and during left ventricular pacing, as well as with left ventricular/right ventricular pacing offsets and differing left ventricular pacing configurations. The pacing measurements are then compared with the distance measurements taken during intrinsic heart rhythm.

If there is no significant improvement in dyssynchrony or significant improvement in shortening fraction, consideration is given to altering the pacing offset, changing the pacing configuration, or changing left or right ventricular lead tip 21*a*, 22*a* position.

Three-dimensional lead tip 21*a*, 22*a* motion analysis may be performed by using simultaneous bi-plane imaging in left anterior oblique (LAO) and right anterior oblique (RAO) views. In the three-dimensional application of the method, the LAO view is adjusted to represent the true short axis of the left ventricle 34 and represents radial shortening. (FIG. 7). The RAO view is obtained at a 90° angle. With simultaneous cine in these two views, the left ventricular lead tip 21*a* motion data is plotted to determine short axis movement (X and Y axis) and right ventricular lead tip 22*a* motion data is plotted to obtain longitudinal motion (Z axis). (FIGS. 15, 16). Using X, Y and Z axis coordinates, three-dimensional left ventricular lead tip 21*a* motion and three dimensional right ventricular lead tip 22*a* motion is determined. Using the three-dimensional technique and analysis thereof, individual lead tip 21*a*, 22*a* motion, dysschrony and fractional shortening can also be determined and graphed.

Three-dimensional lead tip motion analysis may be obtained using a series of topical patches (not shown) applied to the patient's chest (not shown) using a global positioning approach to document the ventricular lead tip 21*a*, 22*a* positions by time. Commercially available motion analysis systems, such as a NAVX system, by St Jude Medical Inc. may be used to perform the three dimensional lead tip motion analysis. The data is collected using the right ventricular lead tip 22*a* as a reference and the left ventricular lead tip 21*a* as input during intrinsic ventricular rhythm and paced ventricular rhythm. Lead tip 21*a*, 22*a* motion is documented during intrinsic heart rhythm and during the paced biventricular rhythm, paced right ventricular rhythm and paced left ventricular rhythm. Other left ventricular pacing configurations and left ventricular/right ventricular pacing offsets may also be documented and assessed. Simultaneous ECG input allows electromechanical measurements of timing from QRS onset to peak mechanical contraction 55 of left or right ventricles 34, 33 respectively during intrinsic and paced rhythms.

Having described our method for optimizing CRT, its operation may be understood.

A patient is identified as having perceived ventricular systolic dyschrony. The patient may be identified by diagnostic use of our method using temporary pacing catheters in the right ventricle 33 and coronary sinus (for left ventricular pacing) similar to a diagnostic electrophysiologic study to assess for baseline dyssynchrony and to predict potential response to CRT.

Alternatively, in a patient identified as a candidate for CRT under the current guidelines, our method may be used to optimize lead tip 21a, 22a, 23a positions and improve CRT response during follow-up.

The first step of the method is the implantation of the leads 21, 22, 23 into the patient's heart H. Initially, the lead tip 21a, 22a, 23a implantation positions are determined empirically using prior studies that have identified the locations typically generating the greatest physiologic benefit from pacing.

The leads 21, 22, 23 are positioned using known catheters and known procedures. As shown in FIG. 1, the atrial lead 23 is positioned in the right atrium with the atrial lead tip 23a affixed to the right atrium 31. The right ventricular lead 22 is positioned in the right ventricle with the right ventricular lead tip 22a attached to the right ventricular apex or septum 47. The left ventricular lead 21 is generally placed in a lateral wall 40 position of the left ventricle 34 via the coronary sinus (allowing for anatomic constraints) or epicardially. The pacemaker or defibrillator 20 is connected to the leads 21, 22, 23 opposite the lead tips 21a, 22a, 23a.

A radiographic imaging system 24 is used to make cine loop image recordings (not shown) of the heart H in the LAO, RAO and AP views (FIG. 17) through at least three complete cardiac cycles during intrinsic heart rhythm. The cine is at a minimum of 15-30 frames per second and time stamps are recorded on each cine frame. The positions of the left ventricular lead tip 21a and the right ventricular lead tip 22a are tracked throughout the cardiac cycles.

The intrinsic rhythm cine loop recordings are converted into an AVI format and transferred to the image compiling system 25, such as a Tracker™ system from Open Sources Physics, Inc. The X-axis, Y-axis and Z-axis coordinates for the left ventricular lead tip 21a and the right ventricular lead tip 22a are determined by the image compiling system 25 and the appropriate time stamps are accorded to each set of coordinates. The compiled data of intrinsic heart rhythm is transferred to the analytical software program 27 to provide a baseline measure of dysschrony and contractility.

The pacemaker 20 is activated and electrical pacing impulses generated within the pacemaker 20 are sent through the leads 21, 22, 23 to the lead tips 21a, 22a, and 23a for paced activation of the heart H. Biventricular pacing, right ventricular pacing and left ventricular pacing may be performed and various left ventricular pacing configurations or left ventricular/right ventricular timing offsets may also be assessed and utilized.

The radiographic imaging system 24 is again used to make cine loop image recordings (not shown) of the heart H in the LAO, RAO and AP views through at least three complete cardiac cycles during the paced heart rhythm configurations. The cine is at a minimum of 15-30 frames per second (fps) and time stamps are recorded on each cine frame. The position of the left ventricular lead tip 21a and the right ventricular lead tip 22a are tracked throughout the cardiac cycles.

The paced rhythm cine loop recordings are converted into an AVI format and transferred to the image compiling system 25. The X-axis, Y-axis and Z-axis coordinates for the left ventricular lead tip 21a and the right ventricular lead tip 22a are determined by the image compiling system 25 and the appropriate time stamps are accorded to each set of coordinates. The compiled results of paced heart rhythm are transferred to the analytical software program 27 to provide a measure of paced dysschrony and contractility.

The analytical software program 27 plots the data from the intrinsic heart rhythm and plots the data from the paced heart rhythm on graphs and generates a visual display 26 showing the motion of the lead tips 21a, 22a by time. The visual display 26 may be printed or electronically displayed graphs and will show the measures of dysschrony and contractility for both intrinsic heart rhythm and the paced heart rhythm.

The visual display is interpreted by the physician performing the procedure to determine if there has been improvement in dysschrony and an improvement in contractility as a result of the pacing.

If assessment of the results shows no significant improvement in contractility or significant improvement in dysschrony, the physician may re-assess pacing with an alternative left ventricular pacing configuration, such as using left ventricular/right ventricular pacing offsets, or move the left ventricular lead tip 21a to another position on the heart H such as to a more atypical position on the lateral wall 40, and/or the physician may change the position of the right ventricular lead tip 22a. The physician may also change offset of the pacemaker 20 to change the timing of the electrical impulses directed to the ventricular lead tips 21a, 22a.

The procedure for making a cine loop recording of the paced heart rhythm is repeated for the new lead tip 21a, 22a positions in the LAO, RAO and AP views and the data is exported for compiling, analysis and comparison against the intrinsic heart rhythm data. If no significant improvement is shown as a result of the new lead tip 21a, 22a position, the procedure may be repeated until improvement is achieved or patient condition requires the procedure be discontinued.

If assessment of the results shows only minimal improvement in contractility or minimal improvement in dysschrony, the physician will record the positions of the lead tips 21a, 22a in the heart H and then may change the positions of the lead tips 21a, 22a to improve the effects of pacing. The procedure for making a cine loop recording of the paced heart rhythm is repeated for the new lead tip 21a, 22a positions in the LAO, RAO and AP views and the data is exported for compiling, analysis and comparison against the intrinsic heart rhythm data. If no significant improvement is shown as a result of the new placement, the procedure may be repeated again or the lead tips 21a, 22a may be repositioned to the earlier position that showed some improvement with pacing.

If assessment of the results shows significant improvement in contractility and significant improvement in dysschrony, the physician will end the procedure.

Use of our method with a three dimensional mapping system such as NAVX (St Jude Medical Inc) allows three dimensional lead tip motion assessment in similar fashion without the detrimental effects of X-ray exposure and also provides ECG correlation as previously described.

This method may also be utilized during routine follow-up of patients with CRT, utilizing external patches and CRT analysis to provide lead tip motion analysis during office reprogramming to maximize CRT therapy.

The foregoing description of our invention is necessarily of a detailed nature so that a specific embodiment of its best mode may be set forth as is require, but it is to be understood that various modifications of details, and rearrangement, substitution and multiplication of steps and apparatus may be resorted to without departing from its spirit, essence or scope.

Having thusly described our invention, what we desire to protect by Letters Patent, and

What we claim is:

1. A method for determining and optimizing left ventricular synchrony during cardiac resynchronization therapy comprising in combination:

identifying a patient as having perceived ventricular systolic dyssynchrony who may benefit from cardiac resynchronization therapy;

implanting left ventricular and right ventricular leads in the patient's heart, each lead having a lead tip at a first end portion;

positioning each lead tip initially at a location prior published studies have shown generate the greatest physiologic benefit from pacing;

connecting a pacemaker to the plural leads opposite the lead tips;

using a radiographic imaging system to make cine loop image recordings of the patient's heart in left anterior oblique, right anterior oblique and anterior-posterior views through at least three complete cardiac cycles during intrinsic heart rhythm and assigning time stamps to each cine frame to ascertain the position of each lead tip throughout the intrinsic cardiac cycles;

transferring the intrinsic rhythm cine loop image recordings to an image compiling system for compiling into intrinsic heart rhythm data and for determining an X-axis, a Y-axis and a Z-axis coordinate for each lead tip for each time stamped cine frame;

transferring the X-axis, the Y-axis and the Z-axis coordinate for each lead tip for each intrinsic rhythm time stamped cine frame to an analytical software program to determine a baseline measure of dyssynchrony and contractility at the current lead tip locations in the patient's heart;

activating the pacemaker to send electrical pacing impulses through the ventricular leads to the lead tips for paced activation of the patient's heart;

using the radiographic imaging system to make cine loop image recordings of the heart in left anterior oblique, right anterior oblique and anterior-posterior views through at least three complete cardiac cycles during the paced heart rhythm and assigning time stamps to each cine frame to ascertain the position of each lead tip throughout the paced cardiac cycles;

transferring the paced rhythm cine loop image recordings to the image compiling system for compiling into paced heart rhythm data and for determining the X-axis, Y-axis and Z-axis coordinate for each lead tip for each paced time stamped cine frame;

transferring the X-axis, the Y-axis and the Z-axis coordinate for each lead tip for each paced rhythm time stamped cine frame to the analytical software program to determine a measure of paced ventricular dyssynchrony and paced ventricular contractility at the current lead tip locations in the patient's heart;

plotting the intrinsic heart rhythm coordinate data and plotting the paced heart rhythm coordinate data and generating a visual display showing the motion of the lead tips by time so that the intrinsic heart rhythm coordinate data may be compared against the paced heart rhythm coordinate data;

interpreting the intrinsic heart rhythm coordinate data and the paced heart rhythm coordinate data to determine if the paced activation of the patient's heart decreases the ventricular dyssynchrony relative to the intrinsic ventricular dyssynchrony and increases ventricular contractility relative to the intrinsic contractility; and ending the cardiac resynchronization therapy if the interpretation of the paced heart rhythm data compared against the intrinsic heart rhythm data shows increased contractility and increased synchrony with paced activation of the patient's heart at the current lead tip locations.

2. The method for determining and optimizing left ventricular synchrony of claim 1 wherein a right ventricular lead tip is located on the patient's heart's right ventricular septum.

3. The method for determining and optimizing left ventricular synchrony of claim 1 wherein a right ventricular lead tip is located on the patient's heart's right ventricular apex.

4. The method for determining and optimizing left ventricular synchrony of claim 1 wherein: a left ventricular lead tip is located on a left ventricular lateral wall.

5. The method for determining and optimizing left ventricular synchrony of claim 1 wherein: a left ventricular lead tip is located on a left ventricular anterolateral wall.

6. The method for determining and optimizing left ventricular synchrony of claim 1 wherein: a left ventricular lead tip is located on a left ventricular posterolateral branch of the coronary sinus.

7. The method for determining and optimizing left ventricular synchrony of claim 1 further comprising:
if interpretation of the results shows no improvement in contractility and no improvement in synchrony, documenting the position of the lead tips in the heart;
changing the position of at least one lead tip; and
repeating the steps of claim 1 for activating the pacemaker, imaging, compiling, identifying coordinate positions and comparing the paced heart rhythm data against the intrinsic heart rhythm data.

8. The method for determining and optimizing left ventricular synchrony of claim 1 further comprising:
if interpretation of the results shows minimal improvement in contractility and minimal improvement in synchrony, documenting the position of the lead tips in the heart;
changing the position of at least one lead tip; and
repeating the steps of claim 1 for activating the pacemaker, imaging, compiling, identifying coordinate positions and comparing the paced heart rhythm data against the intrinsic heart rhythm data.

9. The method for determining and optimizing left ventricular synchrony of claim 1 further comprising:
if interpretation of the results shows minimal improvement in contractility and minimal improvement in synchrony, documenting the position of the lead tips in the heart;
changing the pacing configuration; and
repeating the steps of claim 1 for activating the pacemaker, imaging, compiling, identifying coordinate positions and comparing the paced heart rhythm data against the intrinsic heart rhythm data.

10. The method for determining and optimizing left ventricular synchrony of claim 1 further comprising:
if interpretation of the results shows minimal improvement in contractility and minimal improvement in synchrony, documenting the position of the lead tips in the heart;
changing the ventricular pacing offsets; and
repeating the steps of claim 1 for activating the pacemaker, imaging, compiling, identifying coordinate positions and comparing the paced heart rhythm data against the intrinsic heart rhythm data.

11. The method for determining and optimizing left ventricular synchrony of claim 1 further comprising:
if interpretation of the results shows minimal improvement in contractility and minimal improvement in synchrony, documenting the position of the lead tips in the heart;
changing the timing of the electrical impulses; and repeating the steps of claim 1 for imaging, compiling, identifying coordinate positions and comparing the paced heart rhythm data against the intrinsic heart rhythm data.

12. The method for determining and optimizing left ventricular synchrony of claim 1 further comprising:
using a three dimensional mapping system to generate a three dimensional lead tip motion assessment without the detrimental effects of X-ray exposure to provide ability to determine electromechanical measurements related to dyssynchrony.

13. The method for determining and optimizing left ventricular synchrony of claim 1 wherein:
the method is utilized during routine follow-up care of patients having previously undergone cardiac resynchronization therapy;
using plural topical heart monitor patches to provide three dimensional analysis and the present method to provide lead tip motion analysis during office reprogramming of the pacemaker to maximize long term benefits of cardiac resynchronization therapy.

14. The method for determining and optimizing left ventricular synchrony of claim 1 wherein:
three-dimensional lead tip motion analysis is performed using simultaneous bi-plane imaging in left anterior oblique and right anterior oblique imaging views;
the left anterior oblique view is adjusted to represent short axis of the left ventricle to show radial shortening;
the right anterior oblique view is obtained at a 90° angle;
simultaneous cine is performed in the two views;
the left ventricular lead tip motion data is plotted to determine short axis movement (X and Y axis) and right ventricular lead tip motion data is plotted to obtain longitudinal motion (Z axis);
using the X, Y and Z axis coordinates, three-dimensional left ventricular lead tip motion and three dimensional right ventricular lead tip motion is determined to graph and analyze dyssynchrony and fractional shortening.

15. The method for determining and optimizing left ventricular synchrony of claim 1 wherein:
three-dimensional lead tip motion analysis is obtained using plural topical patches applied to the patient's chest using a global positioning approach to document the ventricular lead tip positions by time;
data is collected using the right ventricular lead tip as a reference and the left ventricular lead tip as input during intrinsic ventricular rhythm and various configurations of paced ventricular rhythm;
lead tip motion is documented during intrinsic heart rhythm and during the paced biventricular rhythm including assessing right and left ventricular pacing offsets, paced right ventricular rhythm and paced left ventricular rhythm, at differing right and left ventricular lead locations; and
simultaneous ECG input provides electromechanical measurements of timing from QRS onset to peak mechanical contraction of left and right ventricles during intrinsic and paced rhythms.

16. The method for determining and optimizing left ventricular synchrony of claim 1 wherein:
the patient is identified as a candidate for cardiac resynchronization therapy by diagnostic use of the method using temporary pacing catheters in the right ventricle and coronary sinus to assess for baseline dyssynchrony and to predict potential response to cardiac resynchronization therapy.

17. The method for determining and optimizing left ventricular synchrony of claim 1 wherein:
the cine is not less than 15 frames per second and time stamps are recorded on each cine frame.

* * * * *